United States Patent [19]

Giroux et al.

[11] 4,124,718

[45] Nov. 7, 1978

[54] ENHANCING ZINC SERUM AND TISSUE LEVELS

[75] Inventors: Eugene L. Giroux; Nellikunja J. Prakash; Paul J. Schechter, all of Strasbourg, France

[73] Assignee: Merrell Toraude et Compagnie, Strasbourg, France

[21] Appl. No.: 765,420

[22] Filed: Jan. 21, 1977

[51] Int. Cl.$^2$ .............................................. A61K 31/40
[52] U.S. Cl. .................................... 424/274; 424/275; 424/285; 424/317
[58] Field of Search ................. 424/274, 275, 285, 317

[56] References Cited

U.S. PATENT DOCUMENTS 3,452,039  6/1969  Buchanan et al. ................... 260/308
3,941,818  3/1976  Abdel-Monem ................. 260/429.9

OTHER PUBLICATIONS

Foye et al. Pharm. Sci. 61 1209 (1972).
Haskel, J. Med. Chem. 13 697 (1970).
Ravazzoni C.A. 57 9833g (1962).
Campaigne et al. J. Org. Chem. 21, 32 (1956).
Halejtrap, Biochem. J. 148 (1) 85 (1974).

*Primary Examiner*—Leonard Schenkman
*Attorney, Agent, or Firm*—Eugene O. Retter; George W. Rauchfuss, Jr.; L. R. Hattan

[57] ABSTRACT

Zinc serum and tissue levels are enhanced by therapeutic administration of certain α-mercapto-β-aryl acrylic acids.

5 Claims, No Drawings

ENHANCING ZINC SERUM AND TISSUE LEVELS

BACKGROUND OF INVENTION

The role of zinc in various agricultural, animal husbandry and animal and human nutritional and therapy requirements has been well established. The need for intervention rather than relying upon chance for adequate zinc provision is apparent as demonstrated by the United States Department of Agriculture survey revealing that the earth in 32 of the states of the United States is zinc deficient. Accordingly, it is common to treat soils or crops with zinc for an optimum harvest.

Domestic animals, zinc enrichment of feed is standard practice in the commercial husbandry of beef and dairy cattle, horses, mice, pheasants, quail poultry, e.g. chickens and turkeys, and fish, catfish and trout. Since zinc deficiency is no general terrestrially, deficiency may also be prevalent in man and other animals particularly in times of increased zinc need.

Zinc is known to be required by at least 18 enzymes and enzyme cofactors including alkaline phosphatase, carbonic anhydrase, carboxypeptidase, dehydrogenases for ethanol, glutamic acid and lactic acid, arginase, carnosinase, dehydropeptidase, glycylglycine, dipeptidase, histidine deaminase, tripeptidase, oxaloacetic carboxylase, lecithinase and enolase.

Zinc deficiency retards growth in cattle, sheep, turkeys, pheasant, chickens, rats, mice and humans. In pigs, calves and poultry, parakeratoses, reddened sore skin and dermatitis are caused by inadequate zinc in the diet. Adequate zinc plasma and tissue levels are necessary to avoid teratogenicity in pregnant animals and to permit egg shell and bone development as well as general growth development and sexual maturation.

While zinc supplement to the diet as by administration of zinc oxide, zinc carbonate, zinc chloride, zinc sulfate, zinc gluconate, zinc lactate, or zinc metal in finely divided form may be advantageous, in man particularly it has been found that the absorption of zinc from the gastrointestinal tract is often inhibited by food material present therein. Diets containing protein or phytic acid from bean, particularly soybean, or cereal, free amino acids or ethylenediamine tetraacetic acid, inactivate or make unavailable the dietary zinc. In various disease conditions, the zinc serum and tissue levels are known to be implicated and enhancing the zinc levels is useful therapy.

Enhanced zinc level has been indicated in the treatment of animals, particularly humans, in burns, serious intestinal fistulas, infarctions, malabsorption, wounds, surgery, dental extraction wounds, idiopathic hypogeusia, venous leg ulcers, decubitus ulcers, syndrome of dwarfism and hypogonadism, while lowered zinc serum and tissue levels are associated with regional enteritis, sickle cell anemia and disease, rheumatoid arthritis, acrodermatitis enteropathica, peptic ulcers, porphyria, hepatic cirrhosis, bone healing, psoriasis, postintubation tracheal granuloma, acute myocardial infarction, renal disease, anemia and geophagia, diabetes mellitus, thalassemia, oral contraception with estrogens, cystic fibrosis, Down's syndrome, pernicious anemia, or corticosteroid antiinflammatory use. In these latter situations where zinc plasma levels have been found to be often lower than normal, raising the zinc plasma and tissue level is thus indicated and has been effective in ameliorating or eliminating some of the disease condition or accelerating healing.

The presently recommended daily adult dietary requirement of zinc is 15 mg. Negative zinc balance ordinarily occurs at an intake of 5 to 6 mg of zinc per day and this is accompanied by the daily loss of about 6 mg of zinc per day by excretion via feces, urine and perspiration. In hot climates the loss in perspiration may amount to 5 mg of zinc per day. While attempts have been made with varying degrees of success to alleviate zinc deficiency in animals and humans by adding a zinc source to the diet, the therapeutic result desired has not been readily achievable because of either the reaction between ionic zinc and gastrointestinal contents or the gastric discomfort occasioned by oral administration of zinc compounds. An attempt to overcome this problem is described in U.S. Pat. No. 3,941,818 issued Mar. 2, 1976 concerned with zinc methionine complexes as a zinc dietary source but does not achieve the dramatic zinc plasma and tissue levels and efficiency obtained by the instant invention even without optional supplementary dietary zinc. In accordance with the present invention, the administration of $\alpha$-mercapto-$\beta$-aryl acrylic acid or its salt facilitates absorption of dietary zinc, dramatically raises the zinc serum and tissue levels and reduces the rate of elimination of zinc from the body.

While $\alpha$-mercapto-$\beta$-aryl acrylic acids are well known, their utilization in therapeutics is exceedingly rare. These compounds are most commonly prepared by the procedure of Campaigne, E. and Cline, R., J. Org. Chem. 21, 32 (1956) from rhodanine and the corresponding aryl aldehyde. U.S. Pat. No. 3,452,039 describes a number of $\alpha$-mercapto-$\beta$-phenylacrylic acids and their substitution products utilized as intermediates in the manufacture of benzothiophene hypocholesterolemic agents. Various $\alpha$-mercapto-$\beta$-substituted arylacrylic acids were prepared and tested by Ravazzoni, C. et al. Ann. Chim. (Rome) 52, 305–12 (1962) Chem. Abst. 57, 9833 g and reported to be effective plant growth substances. Haskel, et al. J. Med. Chem. 13, 697 (1970) prepared and tested $\alpha$-mercapto-$\beta$-aryl acrylic acids including substituted phenyl, substituted thienyl and substituted pyridyl analogs for neuraminidase inhibition and administered the most potent enzyme inhibitors, e.g. $\alpha$-mercapto-$\beta$-4-nitrophenyl acrylic acid orally and intraperitoneally to mice without increase in survival against influenza virus. Being interested in antibacterial and antifungal activity Foy et al., J. Pharm. Sci. 61, 1209 (1972) tested therefor $\alpha$-mercaptocinnamic acid as having some activity in this regard and incidentally relatively weak metal binding avidity for copper, aluminum and iron. Activity in vitro in inhibiting rat heart mitochondria pyruvate transport sensitivity was reported for $\alpha$-thiofuranopyruvate, otherwise named $\alpha$-mercapto-$\beta$-2-furyl, acrylic acid, by Halestrap, A., Biochem. J. 148 (1) 85 (1975) at page 90. No reference more pertinent than these are known to the applicants.

SUMMARY OF INVENTION

This invention relates to a method of enhancing the zinc serum and tissue levels in an animal or human in need thereof by administering to such an $\alpha$-mercapto-$\beta$-arylacrylic acid or its pharmaceutically acceptable non-toxic salt. Administration may be parenterally or orally and zinc may be concurrently administered. The $\alpha$-mercapto-$\beta$-aryl acrylic acid so administered reduces the rate of excretion of zinc, enhances serum and tissue levels of zinc and facilitates absorption of dietary zinc.

This invention also encompasses therapeutic formulations suitable for carrying out the above method, containing α-mercapto-β-arylacrylic acid or salt thereof as an active ingredient.

The α-mercapto-β-arylacrylic acids subject of this invention are restrictedly defined as meaning, in the specification and claims, compounds of the following general Formula I:

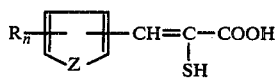

where Z is C=C, O, S or NH; R is H, CH$_3$, C$_2$H$_5$, OH, CH$_3$O, C$_2$H$_5$O, Cl, Br, F, I or CF$_3$; $n$ is 1, 2 or 3; or the pharmaceutically acceptable non-toxic salt thereof.

DETAILED DESCRIPTION OF INVENTION

In animals and humans there are numerous situations which require administration of zinc to overcome disease or promote healing. Other disease conditions are associated with a lower than normal zinc serum and tissue level and, while not established therapy, the treatment of such conditions with a zinc serum and tissue level enhancing agent may be indicated. Particularly suited to such use are the α-mercapto-β-arylacrylic acids of Formula I and their pharmaceutically acceptable non-toxic salts. Further species within the general Formula I are compounds wherein the aryl group is phenyl, or substituted phenyl, e.g. 2,3, or 4-methyl, 2,3 or 4-ethyl, 2,3 or 4-bromo, 2,3 or 4-chloro, 2,3 or 4-fluoro, 2-iodo, 2,4-dichloro, 2,3-dichloro, 2,3,4-trichloro, 2-trifluoromethyl, 3-trifluoromethyl, 2-trifluoromethyl-3-chloro, 2,3 or 4-hydroxy, 2,3 or 4-methoxy, 2,3 or 4-ethoxy, 2-hydroxy-3-methoxy, 3-hydroxy-4-methoxy, 3-methoxy-4-hydroxy, 3-ethoxy-4-hydroxy, 2,3-dimethoxy, 2,4-dimethoxy, 2,5-dimethoxy, 2,6-dimethoxy, 3,4-dihydroxy, 3,4,5-trimethoxy, 2,3,4-trimethoxy, 3,5-dibromo-4-hydroxy; or other aryl groups in place of phenyl, namely 2-furyl, 5-trifluoro-2-furyl; 3-furyl; 2-thienyl, or substituted thienyl e.g. 3-methyl, 5-methyl, 5-ethyl, 5-chloro, 5-bromo, 3-methoxy, 5-methoxy; 3-thienyl; 2-pyrryl; and 3-pyrryl; and the pharmaceutically acceptable non-toxic salts thereof illustratively sodium, potassium, calcium, aluminum, zinc, ammonium salt, amine salt, e.g. trialkylamine, triethylamine, dibenzylamine, glucosamine, of each of the above acids.

Preparation of the α-mercapto-β-arylacrylic acids of applicability herein is according to the method described by Campaigne, E. and Cline, P.E., J. Org. Chem. 21, 32 (1956) by condensing the corresponding carboxaldehyde II with rhodanine III and then splitting the products in alkaline medium, according to the general scheme:

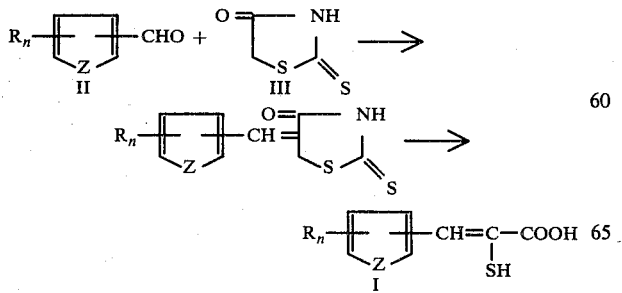

where Z, R and $n$ are as defined in general Formula I. The corresponding carboxaldehydes and their preparation are well known in the art. The desired salts can of course be prepared by reaction between the hydroxide, carbonate or other basic metal, ammonium or amine compound and the free α-mercapto-β-arylacrylic acid in the usual manner.

While there has been some suggestion in the literature that the α-mercapto-β-arylacrylic acids are tautomeric with the thioketo acids, the concensus is that the compounds exist primarily in the mercapto acid form consistent with the chemical and physical properties, Campaigne and Cline, supra.

The compounds of Formula I may be formulated for oral administration as solid or liquid unit dosage forms. The solid dosage forms can be tablets, coated or uncoated; capsules, hard or soft; powders; granules; pills, enteric coated if desired. Solid diluents and carrier may be lactose, starch or other inocuous material with the usual tableting adjuncts as desired. Liquid oral compositions may be dispersions, suspensions, elixirs, syrups or simple solutions in aqueous vehicle. Polyethylene glycols including polyethylene glycol 300 have been found convenient oral vehicles. Unit dosage form as used in the specification and claims means phycially discrete units suitable as unitary administration for humans, each unit containing a predetermined quantity of active ingredient to achieve the desired therapeutic effect in association with a pharmaceutical carrier. Sterile, intraperitoneal formulations with physiologically acceptable vehicle, e.g. saline, optionally buffered can also be utilized.

Administration of the compounds of Formula I, in suitable formulation, is parenterally or preferably orally to an animal, mammal or human in need of enhanced zinc serum and tissue levels. This is not to suggest that in every instance where disease is accompanied by reduced zinc serum and tissue levels that such administration would be effective in ameliorating the disease condition. But where zinc therapy is known to be useful as indicated above, and where the patient, animal or human is in need of zinc therapy and enhanced zinc serum and tissue levels compounds of Formula I can efficatiously be administered.

Dosage rate is widely varied depending upon the need. For human adults the dosage may be about 20 to 30 mg per day, or 0.1 to 2.0 mg per kg of body weight per day, although greater and less amounts also are employable.

The currently accepted method of administering zinc orally utilizes zinc sulfate heptahydrate. Comparisons demonstrate the dramatic superiority of the compounds of Formula I compared to such zinc sulfate. Elevation of zinc serum and tissue levels can be attained with smaller doses of zinc sulfate conjointly administered with the compounds of Formula I as compared with zinc sulfate per se, resulting in reduced gastric irritation.

The following specific examples further illustrate the preparation and utilization of compounds employed in the instant invention.

EXAMPLE 1

α-Mercapto-β-(5-trifluoromethyl-2-furyl)acrylic acid

In a three necked flask, a mixture of 3.4 g of 5-trifluoromethyl-2-furfural, 2.92 g of rhodanine and 5.16 g of dry sodium acetate in 35 ml of glacial acetic acid is stirred and heated to reflux for two hours over a bath at 140°–145° C. After ten minutes a yellow precipitate forms. The reaction mixture is cooled, diluted with 30 ml of water, and the yellow precipitate is filtered, washed with water and dried. After chromatography over silica with dichloromethane as eluent, and recrystallization from dichloromethane and pentane, there is obtained 3.7 g (yield 63%) of yellow crystals of 5-(5-trifluoromethyl-2-furylmethylene)rhodanine. M.P. 174° C. $R_f$ = 0.41 with 3% methanol/dichloromethane on silica gel

| Microanalysis | C | H | N | S |
|---|---|---|---|---|
| Calculated | 38.71 | 1.44 | 5.01 | 22.96 |
| Found | 38.70 | 1.56 | 5.10 | 22.91 |

NMR spectrum in $CDCl_3$
parts per million/tetramethyl silane
6.8 multiplet (ring protons)
7.38 singlet (exocyclic methylene)

1.58 g of the above 5-(5-trifluoromethyl-2-furylmethylene)rhodanine, 23 ml of 1 N sodium hydroxide solution and 25 ml of water are stirred under nitrogen at room temperature for 10 hours. After cooling with an ice bath and acidification with concentrated hydrochloric acid to pH 1.5, the resulting slurry is filtered to yield a slightly brown precipitate which is washed with 50 ml of water by stirring at room temperature under nitrogen and filtered to yield 0.8 g of slightly brown crystals (yield 60%) of α-mercapto-β-(5-trifluoromethyl-2-furyl)acrylic acid. M.P. 158° C.

| Microanalysis | C | H | S |
|---|---|---|---|
| Calculated | 40.34 | 2.11 | 13.46 |
| Found | 40.65 | 2.27 | 13.7 |

NMR is acetone (d 6)
parts per million/tetramethylsilane
7.10 multiplet (ring protons)
7.6 singlet (exocyclic methylene)

EXAMPLE 2

Zinc serum concentration enhanced by oral α-mercapto-β-(2-furyl)acrylic acid

Sprague-Dawley rats were maintained for one week on laboratory ration containing 85 mg of zinc per kg of ration and tap water ad libitum. The evening before the experiment the animals were put on fast and provided only with demineralized water. Rats of 160–190g were randomly distributed between the control and treated groups. The treated group was given by gavage a dose of 25 mg of α-mercapto-β-(2-furyl) acrylic acid (MFA) per kg of body weight. The active compound MFA was dissolved in 50% by volume aqueous polyethylene glycol 300 at a concentration of MFA 5 mg/ml. The control group was similarly dosed with vehicle. Oral dosing of the animals began the following morning and the animals were continued with access only to demineralized water without food. After 4, 6 and 8 hours, blood samples were removed from the animals, allowed to clot, centrifuged and the separated serum recentrifuged and analyzed for zinc content. Zinc was quantified by atomic absorption spectroscopy in solutions from which protein had been precipitated by addition of trichloroacetic acid to a final concentration of 5% (W/V). Results are presented in Table I with the number of rats per group in parenthesis.

TABLE I
Effect of MFA on rat serum zinc concentration

| Hours after dosing | Group | Zinc Concentration μM |
|---|---|---|
| 4 | control (6) | >25 |
|   | treated (5) | 227 |
| 6 | control (6) | 21 |
|   | treated (6) | 252 |
| 8 | control (6) | 24 |
|   | treated (6) | 218 |

Serum zinc concentrations, as shown in Table 1, were increased about ten-fold above the control levels.

EXAMPLE 3

Duration of Activity

Administering MFA by gavage to rats at a dose of 50 mg MFA/kg body weight produced a maximum serum concentration of 14–16 μg zinc/ml at 2–8 hours following dosage compared with untreated rats showing 1.5 μg zinc/ml. The effect on zinc serum persisted for as long as five days after a single dose of MFA, with a decline from maximum seen at 48 hours after gavage.

EXAMPLE 4

Concurrent Administration of Zinc

Serum zinc concentration was determined as a function of time after gavage of 50 mg MFA/kg to rats, after gavage of rats with a mixture of zinc sulfate (10 mg Zn/kg) and MFA (52 mg/kg), and after gavage of zinc sulfate alone (10 mg Zn/kg), using at least five rats for each data point as reported in Table 2.

TABLE 2
Effect of Concurrent Administration of Zinc and MFA on Rat Serum Zinc Concentration

| Hours after dosing | Group | Zinc Concentration μM |
|---|---|---|
| 2 | MFA | 10 |
|   | Zinc sulfate | 4 |
|   | MFA + zinc sulfate | 31 |
| 4 | MFA | 15 |
|   | Zinc sulfate | 2 |
|   | MFA + zinc sulfate | 34.5 |
| 6 | MFA | — |
|   | Zinc sulfate | 1.5 |
|   | MFA + zinc sulfate | — |
| 8 | MFA | 16 |
|   | Zinc sulfate | — |
|   | MFA + zinc sulfate | 35 |
| 48 | MFA | 9 |
|   | Zinc sulfate | — |
|   | MFA + zinc sulfate | 10.5 |

EXAMPLE 5

Decreasing Zinc Excretion

A group of rats was given radioisotropic zinc which was allowed to distribute amongst body zinc pools for nine days. During this period, the six rats in the study were similar to one another in their daily excretion of $^{65}Zn$. On two subsequent mornings, after separate collection of urine and feces, half the group of rats were gavaged with 50 mg MFA/kg, while the other half received vehicle only. The effects of MFA on urinary and fecal elimination of zinc were as reported in Table 3.

TABLE 3

| Day | 24 hour fecal $^{65}$Zn (counts/10 min) | | 24 hour urinary $^{65}$Zn (counts/10 min) | |
|---|---|---|---|---|
| | Control | MFA treated | Control | MFA treated |
| 9 before treatment | 10693 ± 457 | 10640 ± 336 | 95 ± 5 | 107 ± 7 |
| 10 | 9752 ± 288 | 6808 ± 231 | 121 ± 42 | 202 ± 39 |
| 11 | 8511 ± 252 | 3110 ± 358 | 66 ± 22 | 327 ± 81 |

During the two days of MFA treatment, fecal elimination of endogenous zinc was diminished, since only half of the normal elimination of zinc by this route was excreted. Following administration of MFA, urinary excretion of endogenous zinc was elevated but this remained an insignificant source of zinc elimination.

We claim:

1. A method of enhancing zinc serum and tissue levels in a patient in need thereof comprising administering to such patient a therapeutically effective amount of α-mercapto-β-aryl-acrylic acid of the following formula:

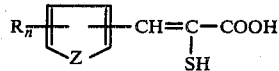

where Z is C=C, O, S or NH; R is H, CH$_3$, C$_2$H$_5$, OH, CH$_3$O, C$_2$H$_5$O, Cl, Br, F, I or CF$_3$; and $n$ is 1, 2 or 3; or the pharmaceutically acceptable non-toxic salt thereof.

2. The method of claim 1 wherein the active ingredient is orally administered α-mercapto-β-phenyl-acrylic acid or the pharmaceutically acceptable non-toxic salt thereof.

3. The method of claim 1 wherein the active ingredient is orally administered α-mercapto-(2-furyl)-acrylic acid or the pharmaceutically acceptable non-toxic salt thereof.

4. The method of claim 1 wherein the active ingredient is orally administered α-mercapto-(2-thienyl)-acrylic acid or the pharmaceutically acceptable non-toxic salt thereof.

5. The method of claim 1 wherein the active ingredient is orally administered α-mercapto-(2-pyrryl)-acrylic acid or the pharmaceutically acceptable non-toxic salt thereof.

* * * * *